United States Patent [19]

Krapcho et al.

[11] Patent Number: 4,952,692

[45] Date of Patent: Aug. 28, 1990

[54] BENZAZEPINE DERIVATIVES

[75] Inventors: John Krapcho, Somerset, N.J.; Joel C. Barrish, Holland, Pa.; Spencer D. Kimball, East Windsor, N.J.

[73] Assignee: E. R. Squibb & Sons, Inc., Princeton, N.J.

[21] Appl. No.: 333,358

[22] Filed: Apr. 4, 1989

[51] Int. Cl.$^5$ ............... C07D 223/16; C07D 281/10; A61K 31/55
[52] U.S. Cl. ................... 540/491; 514/277; 514/213; 540/523
[58] Field of Search ............ 540/491, 523; 514/211, 514/213

[56] References Cited

U.S. PATENT DOCUMENTS

| | | | |
|---|---|---|---|
| 3,562,257 | 2/1971 | Kugita et al. | 540/491 |
| 4,567,175 | 1/1986 | Takeda et al. | 540/491 |
| 4,584,131 | 4/1986 | Floyd et al. | 540/491 |
| 4,590,188 | 5/1986 | Takeda et al. | 540/491 |
| 4,694,002 | 9/1987 | Floyd et al. | 540/491 |
| 4,748,239 | 5/1988 | Floyd et al. | 540/491 |
| 4,752,645 | 6/1988 | Das et al. | 540/491 |

FOREIGN PATENT DOCUMENTS

| | | | |
|---|---|---|---|
| 292840 | 5/1987 | European Pat. Off. | 540/523 |
| 0256888 | 2/1988 | European Pat. Off. | 540/419 |
| 0289241 | 11/1988 | European Pat. Off. | 540/491 |

OTHER PUBLICATIONS

L. H. Werner, et al., "Imidazoline Derivatives with Antiarrhythmic Activity", *J. Med. Chem.*, 1967, 10, 575–582.

*Primary Examiner*—Robert T. Bond
*Attorney, Agent, or Firm*—Theodore R. Furman, Jr.

[57] ABSTRACT

Novel compounds of the formula

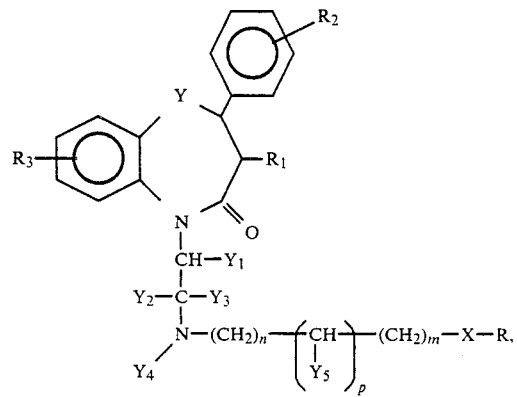

exhibit calcium channel blocking activity and are useful as cardiovascular agents.

24 Claims, No Drawings

BENZAZEPINE DERIVATIVES

SUMMARY OF THE INVENTION

In accordance with the present invention novel compounds having calcium channel blocking activity and which are useful for treating cardiovascular diseases, such as hypertension, are disclosed. These compounds have the general formula

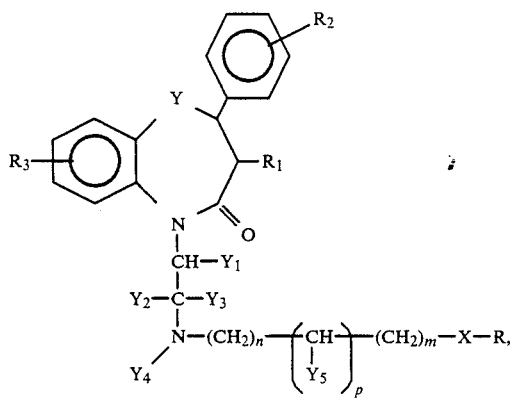

including pharmaceutically acceptable salts thereof, wherein

Y is —$CH_2$— or —S—;
X is —O—, —$S(O)_q$—,

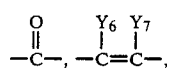

—C≡C—, —NH—,

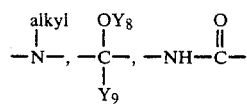

or

R is hydrogen, alkyl, aryl or heteroaryl;
$R_1$ is —CH

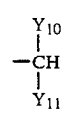

or —O—$Y_{12}$;

$R_2$ and $R_3$ are each independently hydrogen, halogen, alkyl, alkoxy, aryloxy, arylalkoxy, arylalkyl, cyano, hydroxy, alkanoyloxy,

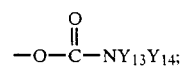

fluoro substituted alkoxy, fluoro substituted alkyl, (cycloalkyl)alkoxy, —$NO_2$, —$NY_{15}Y_{16}$, —$S(O)_q$alkyl, —$S(O)_q$aryl,

or

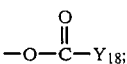

n is 0, 1, 2 or 3;
m is 0, 1, 2 or 3;
p is an integer from 1 to 5;
q is 0, 1 or 2;
$Y_1$, $Y_2$, $Y_3$, $Y_6$ and $Y_7$ are each independently hydrogen or alkyl;
$Y_4$ is selected from hydrogen, alkyl, cycloalkyl or arylalkyl;
$Y_5$ and $Y_9$ are each independently hydrogen, alkyl, aryl or arylalkyl;
$Y_{10}$ and $Y_{11}$ are each hydrogen or alkyl, $Y_{10}$ is hydrogen and $Y_{11}$ is alkenyl, alkynyl, aryl, heteroaryl, or cycloalkyl, or $Y_{10}$ and $Y_{11}$ together with the carbon atom to which they are attached are cycloalkyl;
$Y_8$ and $Y_{12}$ are each independently hydrogen, alkyl, alkanoyl, alkenyl (provided that the double bond is at least 2 carbon atoms away from the oxygen to which $Y_3$ is attached), arylcarbonyl, heteroarylcarbonyl or

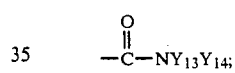

$Y_{13}$ and $Y_{14}$ are each independently hydrogen, alkyl, aryl or heteroaryl, or $Y_{13}$ and $Y_{14}$ together with the nitrogen atom to which they are attached are pyrrolidinyl, piperidinyl, morpholinyl, piperazino or 4-alkylpiperazino;
$Y_{15}$ and $Y_{16}$ are each independently hydrogen, alkyl, alkanoyl, arylcarbonyl, heteroarylcarbonyl, or

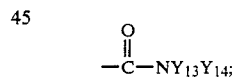

$Y_{17}$ is hydroxy, alkoxy, aryloxy, amino, alkylamino or dialkylamino; and
$Y_{18}$ is alkyl, alkoxy or aryloxy.

DETAILED DESCRIPTION OF THE INVENTION

The definitions below apply to terms as they are used throughout the specification (unless they are otherwise limited in specific instances) either individually or as part of a larger group.

The terms "alkyl" and "alkoxy" refer to both straight and branched chain groups. Those groups having 1 to 10 carbon atoms are preferred.

The term "alkenyl" refers to both straight and branched chain groups. Those groups having 2 to 10 carbon atoms are preferred.

The term "aryl" refers to phenyl and substituted phenyl. Exemplary substituted phenyl groups are phenyl groups substituted with 1, 2 or 3 substituents independently selected from amino (—$NH_2$), alkylamino, dialkylamino, nitro, halogen, hydroxyl, trifluoromethyl, alkyl (of 1 to 4 carbon atoms), alkoxy (of 1 to 4 carbon atoms), alkylthio (of 1 to 4 carbon atoms), alkanoyloxy, carbamoyl or carboxyl groups.

The term "alkanoyl" refers to groups having the formula

Those alkanoyl groups having 2 to 11 carbon atoms are preferred.

The term "heteroaryl" refers to an aromatic heterocyclic group having at least one heteroatom in the ring. Preferred groups are pyridinyl, pyrrolyl, imidazolyl, furyl, thienyl or thiazolyl.

The term "cycloalkyl" refers to groups having 3, 4, 5, 6 or 7 carbon atoms.

The term "halogen" refers to fluorine, chlorine, bromine and iodine.

The terms "fluoro substituted alkyl" and "fluoro substituted alkoxy" refer to alkyl and alkoxy groups (as described above) in which one or more hydrogens have been replaced by fluorine atoms. Exemplary groups are trifluoromethyl, 2,2,2-trifluoroethyl, pentafluoroethyl, fluoromethoxy, difluoromethoxy, etc.

To prepare the compounds of formula I a starting material of the formula

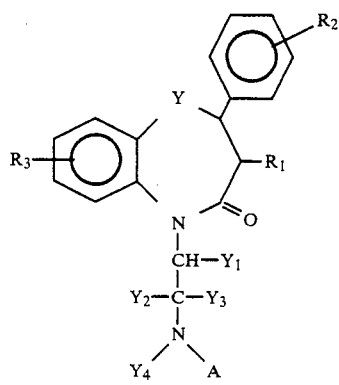

(wherein A is selected from hydrogen, alkyl, cycloalkyl or arylalkyl) with a compound of the formula

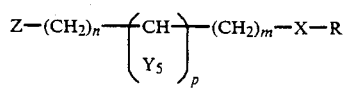

where Z is a leaving group, such as halogen, in one or more solvents such as acetonitrile, butanone dimethylformamide, and in the presence of a base such as potassium carbonate. This is a preferred method.

Compounds of formula II wherein A is hydrogen can be prepared by treatment of compounds of formula II wherein A and $Y_4$ are methyl with trichloroethyl chloroformate in an anhydrous solvent. such as toluene, to give a compound of formula II where A is trichloroethoxycarbonyl. This compound is treated with a reducing agent, such as zinc dust, in a solvent, such as acetic acid, to provide a compound of formula II where A is hydrogen.

The preparation of the compounds of formula II wherein Y is —$CH_2$—, $R_1$ is —O—$Y_{12}$ and $Y_1$, $Y_2$ and $Y_3$ are all hydrogen has been described in U.S. Pat. No. 4,748,239. Starting materials of formula II wherein Y is —$CH_2$—, $Y_1$, $Y_2$ and $Y_3$ are hydrogen and $R_1$ is

can be prepared as described in U.S. Pat. No. 4,752,645. Starting materials of formula II where $Y_1$, $Y_2$ and $Y_3$ are hydrogen and Y is —S— are readily obtainable utilizing prior art methodology as disclosed in U.S. Pat. No. 3,562,257 and Chem. Pharm. Bull. 21:92 (1973).

Compounds of formula II wherein any of $Y_1$, $Y_2$, $Y_3$ are other than hydrogen can be prepared employing the methodology described in U.S. patent application Ser. No. 208,521 filed June 20, 1988. Such methodology involves treating a compound of the formula

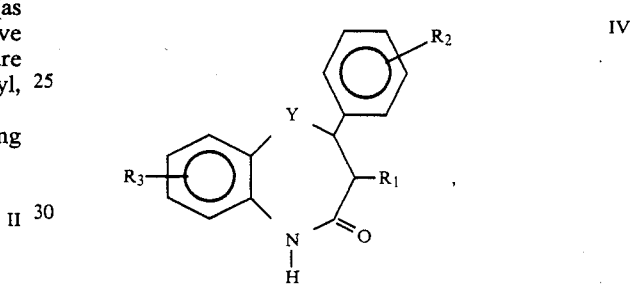

or a salt thereof, such as

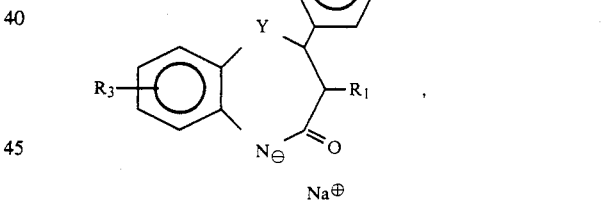

with a base, e.g. sodium hydride, in an inert solvent, e.g. DMF, toluene or DMSO, followed by reaction with a compound of the formula

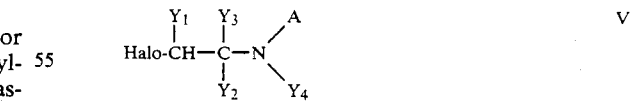

(wherein Halo is halogen, preferably Br or Cl, and A is other than hydrogen) to yield the corresponding product of formula II. Compounds of formula IV and IVa are readily obtainable utilizing the methodology disclosed in the patents discussed above. For example, the preparations of compounds IV and IVa where Y is —$CH_2$— are described in U.S. Pat. No. 4,748,239 in Examples 30 and 43, respectively.

Alternatively, compounds of formula I can be prepared by reacting an aldehyde of the formula

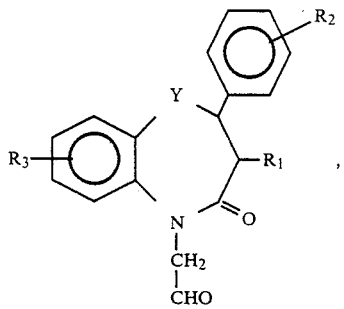

in a solvent, e.q. methanol, with an amine of the formula

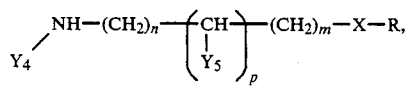

in the presence of hydrogen and a catalyst, e.g. 10% Pd/C. Compounds of formula VI wherein Y is —CH$_2$— are provided, for example, by treating a corresponding compound of formula IV with a base, e.g. sodium hydride, in a solvent such as dimethylformamide, and thereafter treating with an alkylating agent of the formula

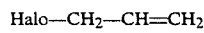

followed by treatment with ozone in a solvent such as methylene chloride.

Another method for preparing compounds of formula I involves treatment of a compound of formula IVa with a base, e.g. sodium hydride, in an inert solvent, e.g. DMF or DMSO, followed by reaction with a compound of the formula

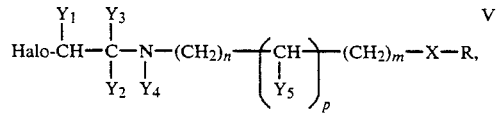

wherein Y$_4$ is other than hydrogen.

Preferred compounds in accordance with the present invention include those wherein R$_1$ is —OH or —O—acetyl;

R$_2$ is hydroxy, alkoxy, alkylthio, alkylamino, aryloxy or arylalkoxy in the 4-position of the phenyl ring;

R$_3$ is 6- or 7-methoxy or 6- or 7-trifluoromethyl;

R is hydrogen or aryl; and

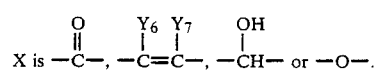

The compounds of formula I form acid-addition salts with inorganic and organic acids. These acid-addition salts frequently provide useful means for isolating the products from reaction mixtures by forming the salt in a medium in which it is insoluble. The free base may then be obtained by neutralization e.g. with a base such as sodium hydroxide. Any other salt may then be formed from the free base and the appropriate inorganic or organic acid. Illustrative are the hydrohalides, especially the hydrochloride and hydrobromide, sulfate, nitrate, phosphate, borate, acetate, tartrate, maleate, citrate, succinate, benzoate, ascorbate, salicylate, methanesulfonate, benzenesulfonate, toluenesulfonate and the like.

The carbon atoms in the 3 and 4-positions of the benzazepine nucleus of the compound of formula I are asymmetric carbons. The carbon atoms in the 2 or 3-positions of the benzothiazepine nucleus of the compound of formula I are also asymmetric carbons. The compounds of formula I therefore exist in enantiomeric and diastereomeric forms and as racemic mixtures thereof. All are within the scope of this invention. It is believed that those compounds of formula I which have the d-cis configuration are the most potent and are therefore preferred.

The compounds of formula I, and the pharmaceutically acceptable salts thereof, are cardiovascular agents. They act as calcium entry blocking vasodilators and are especially useful as anti-hypertensive agents. Thus, by the administration of a composition containing one (or a combination) of the compounds of this invention, the blood pressure of a hypertensive mammalian (e.g., human) host is reduced. A single dose, or two to four divided daily doses, provided on a basis of about 0.1 to 100 milligrams per kilogram of body weight per day, preferably from about 1 to about 50 milligrams per kilogram per day, is appropriate to reduce blood pressure. The substance is preferably administered orally, but parenteral routes such as the subcutaneous, intramuscular or intravenous routes can also be employed.

As a result of the calcium entry blocking activity of the compounds of formula I, and the pharmaceutically acceptable salts thereof, it is believed that such compounds in addition to being hypotensive agents may also be useful as anti-arrhythmic agents, anti-anginal agents, anti-fibrillatory agents, anti-asthmatic agents, anti-ischemic agents and in limiting myocardial infarction.

The compounds of this invention can also be formulated in combination with a diuretic, or a beta-adrenergic agent, or angiotensin converting enzyme inhibitor. Suitable diuretics include the thiazide diuretics such as hydrochlorothiazide and bendroflumethiazide, suitable beta-adrenergic agents include nadolol, and suitable angiotensin converting enzyme inhibitors include captopril.

The compounds of formula I can be formulated for use in the reduction of blood pressure in compositions such as tablets, capsules or elixirs for oral administration, or in sterile solutions or suspensions for parenteral administration. About 10 to 500 milligrams of a compound of formula I is compounded with physiologically acceptable vehicle, carrier, excipient, binder, preservative, stabilizer, flavor, etc., in a unit dosage form as called for by accepted pharmaceutical practice. The amount of active substance in these compositions or preparations is such that a suitable dosage in the range indicated is obtained.

The present invention will now be further described by the following examples, however, it is understood that the invention should not be limited by the details therein.

EXAMPLE 1

(3R-cis)-3-(Acetyloxy)-1,3,4,5-tetrahydro-4-(4-methoxyphenyl)-1-[2-[methyl(2-phenoxyethyl)amino]ethyl]-6-(trifluoromethyl)-2H-1-benzazepin-2-one, monohydrochloride A. (3R-cis)-3-(Acetyloxy)-1,3,4,5-tetrahydro-4-(4-methoxyphenyl)-1-[2-(methylamino)ethyl]-6-(trifluoromethyl)-2H-1-benzazepin-2-one A solution of 3.0 g of (3R-cis)-3-(acetyloxy)-1,3,4,5-tetrahydro-4-(4-methoxyphenyl)-1-[2-(methylamino)ethyl]-6-(trifluoromethyl)-2H-1-benzazepin-2-one, monohydrochloride, prepared as described in U.S. Pat. No. 4,748,239, Example 43, in 15 ml of water was treated with 75 ml of ethyl acetate, followed by the portionwise addition of a solution of 1.3 g of sodium hydrogen carbonate in 10 ml of water. The mixture was shaken and the sl. alkaline aqueous phase was discarded. The organic phase was extracted with 10 ml of water (2×) and then with 10 ml of saturated sodium chloride solution, dried over magnesium sulfate, filtered thorugh a celite bed, and the colorless filtrate was concentrated on a rotary evaporator to give 2.32 g of a colorless solid. The latter was suspended in 15 ml of hexane and filtered to give 2.19 g (90%) of the title A compound as a colorless solid, m.p. 140°–143° C.

Analysis calc'd for $C_{23}H_{25}F_3N_2O_4 \cdot 0.5$ $H_2O$: C, 60.12 H, 5.70; N, 6.10; F, 12.41; Found: C, 60.19; H, 5.37; N, 6.28; F, 12.66.

B. (3R-cis)-3-(Acetyloxy)-1,3,4,5-tetrahydro-4-(4-methoxyphenyl)-1-[2-[methyl(2-phenoxyethyl)amino]ethyl]-6-(trifluoromethyl)-2H-1-benzazpin-2-one, monohydrochloride A stirred mixture of 0.90 g (2 mmol) of the title A compound, 1.20 g (5.9 mmol) of 2-phenoxyethyl bromide and 15 ml of $CH_3CN$ was treated with 0.60 g (4.3 mmol) of potassium carbonate (pulverized). This mixture was stirred and refluxed for 20 hours (TLC indicated the reaction was essentially complete). The solvent was removed on a rotary evaporator and the residue was treated with 150 ml of ethyl acetate and 25 ml of water. The aqueous phase was discarded and the organic layer was extracted with 25 ml of water (2×), dried over magnesium sulfate, filtered and the filtrate was treated with a solution of 0.44 g (4.9 mmol) of oxalic acid in 40 ml of ether. The salt slowly crystallized from solution. After cooling overnight, the product was filtered to give 1.55 g of colorless solid, m.p. 179°–180° C. (foaming).

Analysis calc'd for $C_{31}H_{33}F_3N_2O_5 \cdot C_2H_2O_4$: C, 59.99; H, 5.34; N, 4.24; F, 8.63; Found: C, 59,76; H, 5.29; N, 4.19; F, 8.73.

The oxalic acid salt (1.52 g) was suspended in 25 ml of water and treated with 125 ml of ethyl acetate and 0.80 g of sodium hydrogen carbonate. After shaking in a separatory funnel, the organic phase was separated and extracted twice with 10 ml of water, dried over magnesium sulfate, filtered and the filtrate treated with 0.75 ml of 5.1N hydrochloric acid in EtOH. The resulting solution was concentrated on a rotary evaporation to give a semi-solid. Trituration of the latter with 50 ml of ether gave a granular colorless solid. The solvent was decanted and the solid treated with 30 ml of ether, filtered and dried to give 1.35 g (95%) of the title compound as a colorless hydrochloride, m.p. 90°–100° C. (foaming); $[\alpha]_D^{25°}$ +73.5° (c, 1% MeOH).

Analysis calc'd for $C_{31}H_{33}F_3N_2O_5 \cdot HCl \cdot 0.5$ $H_2O$: C, 60.42; H. 5.73; N, 4.55; Cl, 5.75; Found: C, 60.53; H, 5.86; N, 4.48; Cl, 5.81.

EXAMPLE 2

(3R-cis)-3-(Acetyloxy)-1,3,4,5-tetrahydro-4-(4-methoxyphenyl)-1-[2-[methyl(2-oxo-2-phenylethyl)amino]ethyl]-6-(trifluoromethyl)-2H-1-benzazepin-2-one, monohydrochloride A stirred mixture of 1.35 g (3.0 mmol) of the title A compound from Example 1, 0.93 g (6.0 mol) of phenacyl chloride and 25 ml of $CH_3CN$ was treated with 0.60 g (4.3 mmol) of potassium carbonate (pulverized). This mixture was heated and refluxed for 2 hours (TLC indicated reaction was essentially complete). The reaction mixture was then processed as described in part B of Example 1 to give 1.66 g of the oxalic acid salt, m.p. 90°–100° C. This salt did not crystallize from the usual solvents, combined with 0.29 g from a previous run and converted to the free base (1.69 g). Chromatography of this material on 52 g of Baker's silica gel (60–200 mesh) using 18:1:1 $CH_2Cl_2$—MeOH—AcOH gave 1.42 g of nearly colorless solid. The material was chromatographed again using ethyl acetate to give 0.78 g of nearly colorless foam-like solid. This material was dissolved in 5 ml of $CHCl_3$ and treated with 0.27 ml of 5.1 N hydrochloric acid in ethyl acetate. The solvent was removed on a rotary evaporator to give a granular solid. The latter was triturated with 25 ml of ether, filtered and washed with ether to give 0.63 g of the title compound as a pale yellow solid, m.p. 125°–130° C. (s. 100° C.); $[\alpha]_D^{25°}$ +78.0° (c, 1% MeOH).

Analysis calc'd for $C_{31}H_{31}F_3N_2O_5 \cdot HCl \cdot H_2O$: C, 59.75: H, 5.50; N, 4.50; Cl, 5.69; Found: C, 59.96; H, 5.37; N, 4.50; Cl, 5.65.

EXAMPLE 3

(3R-cis)-3-(Acetyloxy)-1,3,4,5-tetrahydro-4-(4-methoxyphenyl)-1-[2-[methyl(3-oxo-3-phenylpropyl)amino]ethyl]-6-(trifluoromethyl)-2H-1-benzazepin-2-one, monohydrochloride A stirred mixture of 1.35 g (3.0 mmol) of the title A compound of Example 1, 1.28 g (6.0 mmol) of 3-dimethylaminopropiophenone hydrochloride and 25 ml of $CH_3CN$ was treated with 0.83 g (6.0 mmol) of potassium carbonate (pulverized) and heated to reflux (a slow stream of nitrogen was passed over reaction mixture to remove the $HNMe_2$ which was generated). After refluxing for 5 hours (TLC indicated most of the starting material had reacted), the reaction mixture was processed as described in part B of Example 1 to give 2.60 g of the oxalic acid salt. This material was pulverized, suspended in 16 ml of water, filtered and washed with water to give 2.35 g of colorless solid. After this material was again suspended in water (25 ml) and filtered, the product weighed 1.78 g, m.p. 165°–175° C. Converted 1.75 g of this material to the free base (1.38 g). Chromatography of 1.05 g of this material on 30 g of Bakers silica gel (60–200 mesh) with ethyl acetate gave 0.94 g of a colorless foam-like solid. The latter was dissolved in 15 ml of ethyl acetate and treated with 0.32 ml of 5.1 N alcoholic hydrochloric acid. The resulting solution was concentrated on a rotary evaporator to give a colorless foam-like solid. After trituration with 25 ml of ether and cooling overnight, the solid was filtered and washed with ether to give 0.94 g (65%) of the title compound as a solid, m.p. 100°–105° C. (foam); $[\alpha]_D^{25°}$ +75.5° (c, 1% MeOH).

Analysis calc'd for $C_{32}H_{33}F_3N_2O_5 \cdot HCl \cdot H_2O$: C, 60.33; H, 5.70; N, 4.40; Cl, 5.56; Found: C, 60.24; H, 5.66; N, 4.24; Cl, 5.50.

EXAMPLE 4

(3R-cis)-3-(Acetyloxy)-1,3,4,5-tetrahydro-4-(4-methoxyphenyl)-1-[2-[(2-hydroxy-2-phenylethyl)methylamino]ethyl]-6-(trifluoromethyl)-2H-1-benzazepin-2-one, monohydrochloride A stirred mixture of 1.50 g (3.32 mmol) of the title A compound of Example 1 and 2.0 g (16.6 mmol) of styrene oxide was heated in an oil bath at 110°–115° C. Heating was stopped after 2 hours and the cooled material was dissolved in 50 ml of ethyl acetate and treated with a solution of 0.30 g of oxalic acid in 10 ml of ether to give a granular nearly colorless solid. After cooling overnight, the ether was decanted from the solid and the latter triturated with fresh ether and decanted. The entrained solvent was removed on a rotary evaporator giving 2.0 g (91%) of a nearly colorless solid, m.p. 95°–100° C. (s. 80° C.). This material was combined with 0.50 g from a previous run, treated with 25 ml of water and 100 ml of ethyl acetate and then added 0.80 g of sodium hydrogen carbonate portionwise. The mixture was shaken and the sl basic aqueous phase was discarded. The organic phase was extracted with 15 ml of water (2×), 15 ml of sodium chloride solution, dried over magnesium sulfate, filtered and solvent evaporated to give 2.17 g of a nearly colorless foam-like solid, m.p. 55°–100° C. Part of this material (1.07 g) was chromatographed on 32 g of silica (J. T. Baker, 60–200 mesh) using 18:1:1 $CH_2Cl_2$-MeOH-AcOH to give 0.90 g of an oily residue. The latter was treated with 20 ml of ether, filtered to remove the insoluble silica and the filtrate concentrated to give 0.66 g of a foamy solid. It was dissolved in 10 ml of chloroform, filtered to remove a trace of insoluble silica and the solution was treated with 0.23 ml of 5.1 N hydrochloric acid in EtOH. The solution was concentrated on a rotary evaporator to give 0.66 g of a colorless solid. The material was triturated 10 ml of ether, decanted the solvent and the process repeated in order to remove entrained chloroform. The entrained solvent was removed on a rotary evaporator to give 0.51 g (53%) of the title compound as a granular colorless solid, m.p. 95°–100° C. (s. 90° C.); $[\alpha]_D^{25°}$ 82.0° (c, 1% MeOH).

Analysis calc'd for $C_{31}H_{33}F_3N_2O_5 \cdot HCl \cdot 0.5\ H_2O$: C, 60.42; H, 5.73; N, 4.55; Cl, 5.75; Found: C, 60.69; H, 5.66; N, 4.52; Cl, 6.02.

EXAMPLE 5

[3R-[1(1S*,2R*),3α,4α]]-1,3,4,5-Tetrahydro-3-hydroxy-1-[2-[(2-hydroxy-1-methyl-2-phenylethyl)amino]ethyl]-4-(4-methoxyphenyl)-6-(trifluoromethyl)-2H-1-benzazepin-2-one, monohydrochloride A. (3R-cis)-1,3,4,5-Tetrahydro-1-allyl-3-hydroxy-4-(4-methoxyphenyl)-6-(trifluoromethyl)-2H-1-benzazepin-2-one 60% Sodium hydride (0.54 g; 13.5 mmol) was added to (3R-cis)-1,3,4,5-tetrahydro-3-hydroxy- 4-(4-methoxyphenyl)-6-(trifluoromethyl)-2H-1-benzazepin-2-one, (prepared as described in U.S. Pat. No. 4,748,239, Example 30, part F), (5.00 g, 14.2 mmol) in dry dimethyformamide (50 ml) under nitrogen, and the mixture was stirred at room temperature for 20 minutes. The anion mixture was cooled to 0° C. and allyl bromide (1.17 ml; 13.5 mmol) was added and the mixture was stirred overnight, allowing it to gradually reach room temperature. The reaction was quenched with water and extracted with ether (×3). The ether layer was washed with 1N hydrochloric acid (×3), followed by saturated sodium chloride, and was dried over magnesium sulfate and concentrated. After flash chromatography (silica gel/15%–20% ethyl acetate: hexane), 5.45 g of the title A compound as an oil was obtained.

Calc'd for $C_{21}H_{20}NF_3O_3 \cdot 0.53\ H_2O$: C, 62.92; H, 5.29; N, 3.49; Found: C, 63.03; H, 5.25; N, 3.38.

B. (3R-cis)-1,3,4,5-Tetrahydro-1-(formylmethyl)-3-hydroxy-4-(4-methoxyphenyl)-6-(trifluoromethyl)-2H-1-benzazepin-2-one The title A compound (5.32 g; 13.59 mmole) in methanol (140 ml) and methylene chloride (70 ml) was cooled to −78° C. and treated with $O_3$ with stirring. The blue mixture was allowed to stir for 10 minutes and then was flushed with oxygen. The solution was treated with DMS (2 ml) and the solvent was distilled off in the hood. The crude material was flashed (silica gel/2-0%–60% ethyl acetate:hexane), and the isolated material was co-evaporated with hexane (×2) leaving 4.50 g of the title B compound as a white solid, m.p. 64°–68° C.

Calc'd for $C_{20}H_{18}NF_3O_4 \cdot 0.13\ H_2O$: C, 60.70; H, 4.65; N, 3.54; F, 14.40; Found: C, 60.73; H, 4.77; N, 3.27; F, 14.25.

C. [3R-[1(1S*,2R*),3α,4α]]-1,3,4,5-Tetrahydro-3-hydroxy-1-[2-[(2-hydroxy-1-methyl-2-phenylethyl)amino]ethyl]-4-(4-methoxyphenyl)-6-(trifluoromethyl)-2H-1-benzazepin-2-one, monohydrochloride To a 100 ml flask with a magnetic stirrer was added 1.00 g (2.5 mmol) of the title B compound, 0.45 g (3.0 mmol) of (1R,2S)-(−) norephedrine and 10 ml of methanol. To this stirred solution was added a cold slurry of 200 mg of 10% palladium on carbon in 5 ml of methanol. This suspension was placed under a balloon of hydrogen (ca.3 l) and stirred overnight at room temperature. After 17 hours, tlc (10:1 $CH_2Cl_2$—MeOH) indicated about 40% of the title B compound still remained in the reaction mixture. The contents of the flask were filtered (under nitrogen) and washed with methanol. The filtrate was concentrated on a rotary evaporator, dissolved in 10 ml of methanol and treated with a slurry of fresh palladium on carbon (200 mg) in 5 ml of methanol. After stirring for an additional 19 hours, tlc indicated that less than 10% of the title B compound remained in solution. The solution was filtered as above and the filtrate concentrated to give 1.26 g of a granular solid. The latter was dissolved in 70 ml of ethyl acetate and extracted with 5 ml of water (3×). The organic phase was dried over magnesium sulfate, filtered and the filtrate treated with a solution of 0.23 g (2.5 mmol) of oxalic acid in 10 ml of ether. The product rapidly crystallized from solution. After cooling overnight, the colorless solid weighed 1.13 g, m.p. 203°–205° C.

Analysis calc'd for $C_{29}H_{31}N_2F_3O_4 \cdot C_2H_2O_4$: C, 60.19; H, 5.38; N, 4.53; F, 9.21; Found: C, 60.26; H, 5.85; N, 4.80; F, 9.13.

The above material was pulverized, suspended in 15 ml of water and 100 ml of ethyl acetate and treated with 0.40 g of sodium hydrogen carbonate. After vigorous shaking, all of the solid dissolved. The organic phase was washed with 15 mml of water (2×), dried over magnesium sulfate, filtered and the filtrate was treated with 0.37 ml of 5.1 N hydrochloric acid in EtOH. The resulting solution was concentrated on a rotary evaporator to give a syrupy residue. The latter was triturated with 50 ml of ether, cooled and filtered to give 0.91 g (62%) of the title compound as a colorless solid, m.p. 95°–100° C. (foaming); $[\alpha]_D^{25°}$ +68.5° (c, 1% MeOH).

Analysis calc'd for $C_{29}H_{31}F_3N_2O_4 \cdot HCl \cdot H_2O$: C, 59.74; H, 5.88; N, 4.81; Cl, 6.08; Found: C, 59.95; H, 5.88; N, 4.94; Cl, 6.27.

EXAMPLE 6

[3R-[1(1R*,2S*),3α,4α]]-1,3,4,5-Tetrahydro-3-hydroxy-1-[2-[(2-hydroxy-1-methyl-2-phenylethyl)amino]ethyl]-4-(4-methoxyphenyl)-6-(trifluoromethyl)-2H-1-benzazepin-2-one, monohydrochloride Interaction of 0.75 g (1.9 mmol) of the title B compound of Example 5 with 0.29 g (1.9 mmol) of (1S,2R)-(+)-norepinephrine (from the hydrochloric acid salt by treating with potassium carbonate, water and methylene chloride and evaporating the methylene chloride extract) in methanol in the presence of 0.12 g of 10% palladium on carbon according to the procedure described in part C of Example 5 gave 0.50 g of the gelatinous oxalic acid salt. $R_f$ 0.76 (8:1:1 CH₂Cl₂-MeOH-AcOH). This oxalic acid salt was converted to the hydrochloric acid according to the procedure in part C of Example 5 to give 0.30 g of the title compound as a colorless product, m.p. 165°–170° C. (foaming), s. 160; $[\alpha]_D^{25°}$ +86.5° (c, 1% MeOH).

Analysis calc'd for $C_{29}H_{31}F_3N_2O_4 \cdot HCl \cdot H_2O$: C, 59.74; H, 5.85; N, 4.81; Cl, 6.08; Found: C, 59.54; H, 5.90; N, 4.75; Cl, 6.03.

EXAMPLE 7

[3R-[1(S*),3α,4α]]-1,3,4,5-Tetrahydro-3-hydroxy-1-[2-[[2-hydroxy-1-[(4-methoxyphenyl)methyl]amino]ethyl]-4-(4-methoxyphenyl)-6-(trifluoromethyl)-2H-1-benzazepin-2-one, monohydrochloride A. O-methyl ethyl tyrosine hydrochloride 1.50 g (7.68 mmol of O-methyl-L-tyrosine was suspended in 10 ml of absolute EtOH at room temperature. Hydrogen chloride gas was bubbled through the mixture until all of the starting material was in solution. After adding 20 additional ml of EtOH, the mixture was stirred at reflux for 6 hours and then cooled to room temperature. Evaporation gave a light-yellow solid which was recrystallized from methanol/ethyl ether to give 1.69 g of the title A compound as a white solid, m.p. 197°–199° C.

B. (S)-(−)-2-Amino-3-(4-methoxyphenyl)-1-propanol

To a solution of 1.05 g (27.62 mmol) NaBH₄ in 15 ml of 1:1 EtOH/H₂O at room temperature under argon was added a solution of 1.69 g (6.50 mmol) of the title A compound dissolved in 15 ml of 1:1 EtOH/H₂O. The resulting solution was stirred at reflux for 5 hours and then cooled to room temperature and the EtOH evaporated. The remaining solid and water was extracted with 2×50 ml of ethyl acetate. The organic layer was dried (Na₂SO₄) and evaporated to give 0.95 g of the title B compound as a white solid.

C. [3R-[1(S*),3α,4α]]-1,3,4,5-Tetrahydro-3-hydroxy-1-[2-[[2-hydroxy-1-[(4-methoxyphenyl) methyl]amino]ethyl]-4-(4-methoxyphenyl)-6-(trifluoromethyl)-2H-1-benzazepin-2-one, monohydrochloride To a solution of 1 g (2.54 mmol) of the aldehyde of part B of Example 5 in 25 ml of methanol was added 0.55 g (3.05 mmol) of the title B compound followed by 0.125 g of 10% palladium on carbon and the resulting suspension stirred at room temperature under an atmosphere of hydrogen (balloon) for 20 hours. The reaction mixture was filtered through a pad of celite and evaporated. The resulting oil was recharged with methanol, catalyst, and an additional 0.14 g of the primary amine as above and stirred for an additional 24 hours. The reaction was worked up as above and purified by flash chromatography to give 1.26 g of a white foam. This was dissolved in 100 ml of ethyl acetate. A solution of 300 mg of oxalic acid in 25 ml of ether was added to make the oxalate salt which was recrystallized from hot CH₃CN. Saturated HCl/Et₂O was added to a solution of the regenerated free base dissolved in 25 ml of dry ethyl ether which was evaporated and dried to give 603 mg of the title compound as a white amorphous solid, m.p. 120°–124° C.; $[\alpha]_D^{25°}$ 76.8° (c, 1% MeOH).

Analysis calc'd for $C_{30}H_{34}ClF_3N_2O_5 \cdot 0.3\ H_2O$: C, 60.01; H, 5.81; Cl, 5.90; F, 9.49; N, 4.67; Found: C, 59.99; H, 5.70; Cl, 5.94; F, 9.47; N, 4.63.

EXAMPLE 8

(R-cis)-3-(Acetyloxy)-1,3,4,5-tetrahydro-4-(4-methoxyphenyl)-1-[2-[methyl(3-phenyl-2-propenyl)amino]ethyl]-6-(trifluoromethyl)-2H-1-benzazepin-2-one, monohydrochloride A stirred mixture of 0.86 g (1.9 mmol) of the title A compound from Example 1 and 15 ml of CH₃CN was treated with a solution of 0.40 g (2.6 mmol) of cinnamyl chloride in 5 ml of CH₃CN, followed by 0.30 g of potassium carbonate (pulverized), and then refluxed for 3 hours. The reaction mixture was processed as described in part B of Example 1 to give 1.12 g of the oxalic acid salt. The latter was converted to the free base (1.0 g) and chromatographed on 30 g of Baker's silica gel (60–200 mesh) using 1:1 ethyl acetate-hexane to give 0.78 g of a foamy solid. This material was dissolved in 10 ml of ethyl acetate and treated with a solution of 0.27 ml of 5.1 N hydrochloric acid in EtOH. The solution was concentrated on a rotary evaporator to give a foamy colorless solid which was triturated with 20 ml of ether to give a granular solid. After standing overnight in the cold, the solvent was decanted and the solid again triturated with 10 ml of ether and decanted. The entrained solvent was removed under high vacuum to give 0.78 g of the title compound as a colorless free-flowing solid, m.p. 100°–105° C. (foam), s. 85°; $[\alpha]_D^{25°}$ 72.2° (c, 1% MeOH).

Analysis calc'd for $C_{32}H_{33}F_3N_2O_4 \cdot HCl \cdot 0.75\ H_2O$: C, 62.34; H, 5.80; N, 4.54; Cl, 5.75; Found: C, 62.45; H, 5.87; N, 4.43; Cl, 5.82.

EXAMPLE 9

[3R-[1(R*),3α,4α]]-1,3,4,5-Tetrahydro-3-hydroxy-1-[2-[[1-(hydroxymethyl)-2-phenylethyl]amino]ethyl]-4-(4-methoxyphenyl)-6-(trifluoromethyl)-2H-1-benzazepin-2-one, monohydrochloride To a solution of 1 g (2.54 mmol) of aldehyde of part B of Example 5 in 25 ml of methanol was added 0.42 g (2.80 mmol) (R)-(+)-2-amino-3-phenyl-1-propanol followed by 0.125 g of 10% palladium on carbon and the resulting suspension stirred at room temperature under an atmosphere of hydrogen for 18 hours. The reaction mixture was filtered through a pad of celite and evaporated. The resulting oil was recharged with methanol, catalyst and an additional 100 mg of the primary amine as above and stirred for an additional 24 hours. The reaction was worked up as above and purified by flash chromatography to give 1.18 g of a white foam. This was dissolved in 50 ml of ethyl acetate. A solution of 0.14 g of oxalic acid in 25 ml of ether was added to make the oxylate salt which was recrystallized from ethyl acetate. Saturated hydrochloric acid/ethyl ether was added to a solution of the regenerated free base dissolved in 25 ml of dry ethyl ether which was evaporated and dried to give 725 mg of the title compound as a white amorphous, hygroscopic solid, m.p. 125°–130° C.; $[\alpha]_D^{25°}$ +98.1° (c, 1% MeOH).

Analysis calc'd for $C_{29}H_{32}ClF_3N_2O_4$: C, 61.64; H, 5.71; Cl, 6.27; F, 10.09; N, 4.96; Found: C, 61.25; H, 5.97; Cl, 6.63; F, 10.37; N, 4.92.

Example 10

[3R-[1(S*),3α,4α]]-1,3,4,5-Tetrahydro-3-hydroxy-1-[2-[[1-(hydroxymethyl)-2-phenylethylethyl]amino]ethyl]-4-(4-methoxyphenyl)-6-(trifluoromethyl)-2H-1-benzazepin-2-one, monohydrochloride To a solution of 1 g (2.54 mmol) of aldehyde of part B of Example 5 in 25 ml of methanol was added 0.42 g (2.80 mmol) of (S)-(−)-2-amino-3-phenyl-1-propanol followed by 0.125 g of palladium on carbon and the resulting suspension stirred at room temperature under an atmosphere of hydrogen for 22 hours. The reaction mixture was filtered through a pad of celite and evaporated. The resulting oil was recharged with methanol, catalyst and an additional 200 mg of the primary amine as above and stirred for an additional 24 hours. The reaction was worked up as above and purified by flash chromatography to give 1.22 g of a white foam.

Saturated hydrochloric acid/ethyl ether was added to a solution of 1.22 g (2.33 mmol) of the above amine (white foam) in 25 ml of dry ethyl ether to give 0.95 g of the title compound hydrochloride salt as a white amorphous solid, m.p. 125°–133° C.; $[\alpha]_D^{25°}$ +76.1° (c,1% MeOH).

Analysis calc'd for $C_{29}H_{32}ClF_3N_2O_4 \cdot 0.26\ H_2O$: C, 61.14; H. 5.75; Cl, 6.22; F, 10.01; N, 4.92; Found: C, 61.23; H, 5.86; Cl, 5.84; F, 9.69; N, 4.83.

EXAMPLE 11

(3R-cis)-1,3,4,5-Tetrahydro-3-hydroxy-1-[2-[(3-hydroxypropyl)amino]ethyl]-4-(4-methoxyphenyl)-6-(trifluoromethyl)-2H-1-benzazepin-2-one, monohydrochloride A stirred mixture of 1.00 g (2.5 mmol of the title B compound of Example 5, 0.23 g (3.0 mmol) of 3-amino-1-propanol and 10 ml of methanol was treated with a cold slurry of 200 mg of 10% palladium on carbon in 5 ml of methanol and placed under a balloon of hydrogen. After stirring for 23 hours, the mixture was process as described in part C of Example 5 to give 1.10 g of the oxalic acid salt, m.p. 201°–202° C. (foaming, red melt).

The oxalic acid salt was pulverized, suspended in 20 ml of water, 75 ml of ethyl acetate and 0.4 g of sodium hydrogen carbonate. The mixture was shaken vigorously and the layers separated. The aqueous slurry was extracted with 50 ml of ethyl acetate (2×) and the organic phases were combined, washed with 20 ml of water, dried over magnesium sulfate, filtered and solvent evaporated to give 0.88 g of the base. The latter was dissolved in 20 ml of CHCl₃ and treated with 0.39 ml of 5.1 N alcoholic hydrochloric acid. This solution was diluted with 25 ml of ether to give a colorless crystalline solid. After cooling overnight, the solid was filtered and washed with ether to give 0.84 g of the title compound, m.p. 156°–159° C.; $[\alpha]_D^{25°}$ 84.6° (c, 1% MeOH).

Analysis calc'd for $C_{23}H_{27}F_3N_2O_4 \cdot HCl \cdot 0.5\ H_2O$: C, 55.46; H, 5.87; N, 5.63; Cl, 7.12; Found: C, 55.69; H, 5.82; N, 5.59; Cl, 6.97.

EXAMPLE 12

(3R-cis)-3-(Acetyloxy)-1,3,4,5-tetrahydro-4-(4-methoxyphenyl)-1-[2-[methyl(2-phenylthioethyl)-amino]ethyl]-6-trifluoromethyl-2H-1-benzazepin-2-one monohydrochloride Following the procedure of Example 1, part B, but substituting 2-phenylthioethyl bromide for the 2-phenoxyethyl bromide, the title compound was obtained.

EXAMPLE 13

(3R-cis)-3-(Acetyloxy)-1,3,4,5-tetrahydro-4-(4-methoxyphenyl)-1-2-[methyl(phenylaminoethyl)amino]-ethyl]-6-trifluoromethyl-2H-1-benzazepin-2-one monohydrochloride Following the procedure of Example 1, part B, but substituting 2-phenylaminoethyl chloride for the 2-phenoxyethyl bromide, the title compound was obtained.

EXAMPLE 14

(3R-cis)-3-(Acetyloxy)-1,3,4,5-tetrahydro-4-(4-methoxyphenyl)-1-2-[methyl(benzoylaminoethyl)amino]ethyl]-6-trifluoromethyl-2H-1-benzazepin-2-one monohydrochloride Following the procedure of Example 1, part B, but substituting 2-benzoylaminoethyl chloride for 2-phenoxyethyl bromide, the title compound was obtained.

EXAMPLE 15

(3R-cis)-3-(Acetyloxy)-2,3-dihydro-2-(4-methoxyphenyl)-5-[2-[methyl(2-phenoxyethyl)amino]ethyl-1,5-benzothiazepin-4(5H)-one, monohydrochloride Following the procedure of Example 1, part B, but substituting (3R-cis)-3-(acetyloxy)-2,3-dihydro-2-(4-methoxyphenyl)-5-[2-(methylamino)ethyl]-1,5-benzothiazepin-4(5H)-one for the (3R-cis)-3-(acetyloxy)-1,3,4,5-tetrahydro-4-(4-methoxyphenyl)-1-[2-(methylamino)ethyl]-6-(trifluoromethyl)-2H-1-benzazepin-2-one, the title compound was obtained.

EXAMPLE 16

(3R-cis)-3-(Acetyloxy)-2,3-dihydro-2-(4-methoxyphenyl)-5-[2-[methyl(3-oxo-3-phenylpropyl)amino]-ethyl]-1,5-benzothiazepin-4(5H)-one, monohydrochloride Following the procedure of Example 3 but substituting (3R-cis)-3-(acetyloxy)-2,3-dihydro-2-(4-methoxyphenyl)-5-[2-(methylamino)ethyl-1,5-benzothiazepin-4(5H)-one for the (3R-cis)-3-(acetyloxy)-1,3,4,5-tetrahydro-4-(4-methoxyphenyl)-1-[2-(methylamino)ethyl-6-trifluoromethyl)-2H-1-benzazepin-2-one, the title compound was obtained.

EXAMPLE 17

(3R-cis)-3-(Acetyloxy)-2,3-dihydro-2-(4-methoxyphenyl)-5-[2-[methyl(3-phenyl-2-propenyl)amino]ethyl]-1,5-benzothiazepin-4-one, monohydrochloride Following the method of Example 8 but substituting (3R-cis)-3-(acetyloxy)-2,3-dihydro-2-(4-methoxyphenyl)-5-[2-methylamino)ethyl.-1,5-benzothiazepin-4(5H)-one for the (3R-cis)-3-(acetyloxy)-1,3,4,5-tetrahydro-4-(4-methoxyphenyl]-1-2-(methylamino)ethyl]-6-trifluoromethyl)-2H-1-benzazepin-2-one, the title compound was obtained.

What is claimed is:

1. A compound of the formula

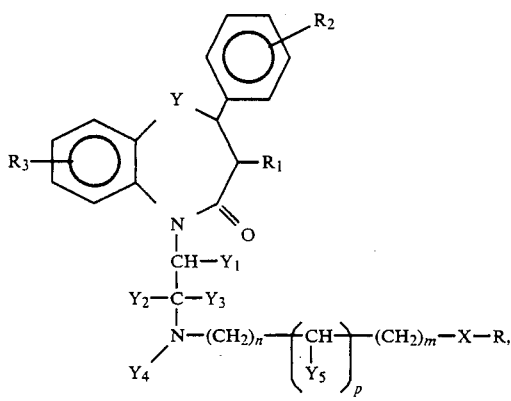

including pharmaceutically acceptable salts thereof wherein

Y is —CH$_2$— or —S—;
X is —O—, —S(O)$_q$—,

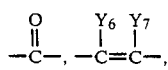

—C≡C—, —NH—,

or

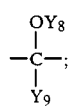

R is hydrogen, alkyl, aryl or heteroaryl;
R$_1$ is

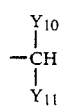

or —O—Y$_{12}$;

R$_2$ and R$_3$ are each independently hydrogen, halogen, alkyl, alkoxy, aryloxy, arylalkoxy, diarylalkoxy, arylalkyl, cyano, hydroxy, alkanoyloxy,

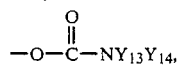

fluoro substituted alkoxy, fluoro substituted alkyl, (cycloalkyl)-alkoxy, —NO$_2$, —NY$_{15}$Y$_{16}$, —S(O)$_q$alkyl, —S(O)$_q$aryl,

or

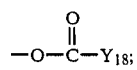

n is 0, 1, 2 or 3;
m is 0, 1 or 2;
p is an integer from 1 to 5;
q is 0, 1 or 2;
Y$_1$, Y$_2$, Y$_3$, Y$_6$ and Y$_7$ are each independently hydrogen or alkyl;
Y$_4$ is selected from hydrogen, alkyl, cyclo-alkyl or arylalkyl;
Y$_5$ and Y$_9$ are each independently hydrogen, alkyl, aryl or arlalkyl;
Y$_{10}$ and Y$_{11}$ are each hydrogen or alkyl, Y$_{10}$ is hydrogen and Y$_{11}$ is alkenyl, alkynyl, aryl, heteroaryl, or cycloalkyl, or Y$_{10}$ and Y$_{11}$ together with the carbon atom to which they are attached are cycloalkyl;
Y$_8$ and Y$_{12}$ are each independently hydrogen, alkyl, alkanoyl, alkenyl (provided that the double bond is at least 2 carbon atoms away from the oxygen to which Y$_3$ is attached), arylcarbonyl, heteroarylcarbonyl or

Y$_{13}$ and Y$_{14}$ are each independently hydrogen, alkyl, aryl ox heteroaryl, or Y$_{13}$ and Y$_{14}$ together with the nitrogen atom to which they are attached are pyrrolidinyl, piperidinyl or morpholinyl;
Y$_{15}$ and Y$_{16}$ are each independently hydrogen, alkyl, alkanoyl, arylcarbonyl, heteroarylcarbonyl, or

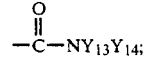

Y$_{17}$ is hydroxy, alkoxy, aryloxy, amino, alkylamino or dialkylamino; and
Y$_{18}$ is alkyl, alkoxy or aryloxy;
wherein the terms "alkyl" and "alkoxy" refer to both straight and branched chain groups having 1 to 10 carbon atoms;
the term "alkenyl" refers to both straight and branched chain groups having 2 to 10 carbon atoms;
the term "aryl" refers to phenyl and substituted phenyl wherein the 1, 2 or 3 substutuents are independently selected from amino, alkylamino, dialkylamino, amino, nitro, halogen, hydroxyl, trifluoromethyl, alkyl of 1 to 4 carbon atoms, alkoxy of 1 to 4 carbon atoms, alkylthio of 1 to 4 carbon atoms, alkanoyloxy, carbamoyl or carboxyl groups;

the term "alkanoyl" refers to groups having the formula

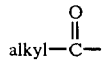

and having 2 to 11 carbon atoms;

the term "heteroaryl" refers to groups selected from pyridinyl, pyrrolyl, imidazolyl, furyl, thienyl and thiazolyl;

the term "cycloalkyl" refers to groups having 3, 4, 5, 6 or 7 carbon atoms;

the term "halogen" refers to fluorine, chlorine, bromine and iodine; and the terms "fluoro substituted alkyl" and "fluoro substituted alkoxy" refer to alkyl and alkoxy groups in which one or more hydrogens have been replaced by fluorine atoms.

2. A compound in accordance with claim 1 wherein
$R_1$ is —OH or —O—acetyl;
$R_2$ is hydroxy, alkoxy, alkylthio, alkylamino, aryloxy or arylalkoxy in the 4-position of the phenyl ring;
$R_3$ is 6- or 7-methoxy or 6- or 7-trifluoromethyl;
R is hydrogen or aryl; and
X is

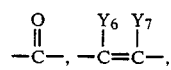

or —O—.

3. A compound in accordance with claim 1 wherein
$R_1$ is

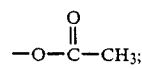

$R_2$ is 6-trifluoromethyl;
$R_3$ is 4-methoxy;
Y is —CH$_2$—;
$Y_4$ is —CH$_3$;
X is —O—,

or

and
R is phenyl.

4. A compound in accordance with claim 1 wherein
$R_1$ is —OH;
$R_2$ is 6-trifluoromethyl;
$R_3$ is 4-methoxy;
Y is —CH$_2$—
$Y_4$ is hydrogen;
$Y_5$ is —CH$_3$;
X is

and
R is phenyl.

5. A compound in accordance with claim 1 wherein
R is —OH;
$R_2$ is 6-trifluoromethyl;
$R_3$ is 4-methoxy;
Y is —CH$_2$—
$Y_4$ is hydrogen;
$Y_5$ is

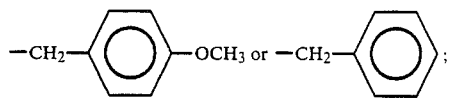

X is oxygen; and
R is hydrogen.

6. A compound in accordance with claim 1 wherein
$R_1$ is

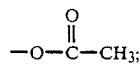

$R_2$ is 6-trifluoromethyl;
$R_3$ is 4-methoxy;
Y is —CH$_2$—
$Y_4$ is methyl;
X is

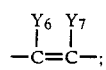

and
R is phenyl.

7. A compound in accordance with claim 1 wherein
$R_1$ is —OH;
$R_2$ is 6-trifluoromethyl;
$R_3$ is 4-methoxy;
Y is —CH$_2$—
$Y_4$ is hydrogen;
X is oxygen; and
R is hydrogen.

8. A compound in accordance with claim 1 wherein (3R-cis)-3-(acetyloxy)-1,3,4,5-tetrahydro-4-(4-methoxyphenyl)-1-[2-[methyl(2-phenoxyethyl)amino]ethyl]-6-(trifluoromethyl)-2H-1-benzazepin-2-one, monohydrochloride.

9. A compound in accordance with claim 1 wherein (3R-cis)-3-(acetyloxy)-1,3,4,5-tetrahydro-4-(4-methoxyphenyl)-1-[2-[methyl(2-oxo-2-phenylethyl)amino]ethyl]-6-(trifluoro-methyl)-2H-1-benzazepin-2-one, monohydrochloride.

10. A compound in accordance with claim 1 wherein (3R-cis)-3-(acetyloxy)-1,3,4,5-tetrahydro-4-(4-methoxyphenyl)-1-[2-[methyl(3-oxo-3-phenylpropyl)amino]ethyl]-6-(trifluoromethyl)-2H-1-benzazepin-2-one, monohydrochloride.

11. A compound in accordance with claim 1 wherein (3R-cis)-3-(acetyloxy)-1,3,4,5-tetrahydro-4-(4-methoxyphenyl)-1-[2-[(2-hydroxy-2-phenylethyl)methylamino]ethyl]-6-(trifluoromethyl)-2H-1-benzazepin-2-one, monohydrochloride.

12. A compound in accordance with claim 1 wherein [3R-[1(1S*,2R*),3α,4α]]-1,3,4,5-tetrahydro-3-hydroxy-1-[2-[(2-hydroxy-1-methyl-2-phenylethyl)amino]ethyl]-4-(4-methoxyphenyl)-6-(trifluoro-methyl)-2H-1-benzazepin-2-one, monohydrochloride.

13. A compound in accordance with claim 1 wherein [3R-[1(1R*,2S*),3α,4α]]-1,3,4,5-tetrahydro-3-hydroxy-1-[2-[(2-hydroxy-1-methyl-2-phenylethyl)amino]ethyl]-4-(4-methoxyphenyl)-6-(trifluoro-methyl)-2H-1-benzazepin-2-one, monohydrochloride.

14. A compound in accordance with claim 1 wherein [3R-[1(S*),3α,4α]]-1,3,4,5-tetrahydro-3-hydroxy-1-[2-[[2-hydroxy-1-[(4-methoxyphenyl)methyl]amino]ethyl]-4-(4-methoxyphenyl)-6-(trifluoromethyl)-2H-1-benzazepin-2-one, monohydrochloride.

15. A compound in accordance with claim 1 wherein (R-cis)-3-(acetyloxy)-1,3,4,5-tetrahydro-4-(4-methoxyphenyl)-1-[2-[methyl(3-phenyl-2propenyl)amino]ethyl]-6-(trifluoromethyl)-2H-1-benzazepin-2-one, monohydrochloride.

16. A compound in accordance with claim 1 wherein [3R-[1(R*),3α,4α]]-1,3,4,5-tetrahydro-3-hydroxy-1-[2-[[1-(hydroxymethyl)-2-phenylethyl]amino]ethyl]-4-(4-methoxyphenyl)-6-(trifluoromethyl)-2H-1-benzazepin-2-one, monohydrochloride.

17. A compound in accordance with claim I wherein [3R-[1(S*),3α,4α]]-1,3,4,5-tetrahydro-3-hydroxy-1-[2-[1-(hydroxymethyl)-2-phenylethyl]amino]ethyl]-4-(4-methoxyphenyl)-6-(trifluoromethyl)-2H-1-benzazepin-2-one, monohydrochloride.

18. A compound in accordance with claim 1 wherein (3R-cis)-1,3,4,5-tetrahydro-3-hydroxy-1-[2-[(3-hydroxypropyl)amino]ethyl]-4-(4-methoxyphenyl)-6-(trifluoromethyl)-2H-1-benzazepin-2-one, monohydrochloride.

19. A compound in accordance with claim 1 wherein (3R-cis)-3-(Acetyloxy)-1,3,4,5-tetrahydro-4-(4-methoxyphenyl)-1-[2-[methyl(2-phenylthioethyl)amino]ethyl]-6-trifluoromethyl-2H-1-benzazepin-2one monohydrochloride.

20. A compound in accordance with claim 1 wherein (3R-cis)-3-(Acetyloxy)-1,3,4,5-tetrahydro-4-(4-methoxyphenyl)-1-2-[methyl(phenylaminoethyl)amino]ethyl]-6-trifluoromethyl-2H-1-benzazepin-2one monohydrochloride.

21. A compound in accordance with claim 1 wherein (3R-cis)-3-(Acetyloxy)-1,3,4,5-tetrahydro-4-(4-methoxyphenyl)-1-2-[methyl(benzoylaminoethyl)amino]ethyl]-6-trifluoromethyl-2H-1-benzazepin-2-one monohydrochloride 22. A compound in accordance with claim 1 wherein (3R-cis)-3-(Acetyloxy)-2,3-dihydro-2-(4-methoxyphenyl)-5-[2-[methyl(2-phenoxyethyl)amino]ethyl-1,5-benzothiazepin-4(5H)-one, monohydrochloride.

23. A compound in accordance with claim 1 wherein (3R-cis)-3-(Acetyloxy)-2,3-dihydro-2-(4-methoxyphenyl)-5-[2-[methyl(3-oxo-3-phenylpropyl)amino]ethyl]-1,5-benzothiazepin-4(5H)-one, monohydrochloride.

24. A compound in accordance with claim 1 wherein (3R-cis)-3-(Acetyloxy)-2,3-dihydro-2-(4-methoxyphenyl)-5-[2-[methyl(3-phenyl-2-propenyl)amino]ethyl]-1,5-benzothiazepin-4-one, monohydrochloride.

* * * * *